United States Patent [19]

Kanba et al.

[11] Patent Number: 5,062,292

[45] Date of Patent: Nov. 5, 1991

[54] DEVICE FOR MEASURING GAS DISSOLVED IN OIL

[75] Inventors: Masaru Kanba; Yasuo Inoue; Sadayoshi Mukai; Masanari Kikkawa; Yasunori Suga, all of Kyoto, Japan

[73] Assignee: Nissin Electric Co., Ltd., Kyoto, Japan

[21] Appl. No.: 520,842

[22] Filed: May 8, 1990

Related U.S. Application Data

[63] Continuation of Ser. No. 231,296, Aug. 12, 1988, abandoned.

[30] Foreign Application Priority Data

| Aug. 12, 1987 | [JP] | Japan | 62-123564[U] |
| Aug. 17, 1987 | [JP] | Japan | 62-125089[U] |
| Dec. 25, 1987 | [JP] | Japan | 62-198513[U] |
| Dec. 29, 1987 | [JP] | Japan | 62-198878[U] |
| Feb. 12, 1988 | [JP] | Japan | 63-18026[U] |
| Apr. 18, 1988 | [JP] | Japan | 63-51682[U] |

[51] Int. Cl.$^5$ ............................................. G01N 7/00
[52] U.S. Cl. ..................... 73/19.01; 73/19.1; 73/23.35; 73/61 R
[58] Field of Search ............. 73/19.1, 19.01, 23.35, 73/61 R; 55/53, 196

[56] References Cited

U.S. PATENT DOCUMENTS

| 2,112,845 | 4/1938 | Howell | 73/19.1 |
| 2,987,912 | 6/1961 | Jacobson | 73/19 |
| 3,942,792 | 3/1976 | Topol | 73/19 |
| 4,236,404 | 12/1980 | Ketchum et al. | 73/19 |
| 4,266,950 | 5/1981 | Makino et al. | 55/196 |
| 4,330,385 | 5/1982 | Arthur et al. | 73/23 |
| 4,402,211 | 9/1983 | Sugawara et al. | 73/19 |
| 4,444,040 | 4/1984 | Sakai et al. | 73/19 |
| 4,546,640 | 10/1985 | Stone et al. | 73/19 |
| 4,612,020 | 9/1986 | Fischer et al. | 55/196 |
| 4,699,886 | 10/1987 | LeLong | 73/863.21 |
| 4,763,514 | 8/1988 | Naito et al. | 73/19 |
| 4,764,344 | 8/1988 | Knab | 73/19 |
| 4,849,178 | 7/1989 | Azuma | 73/61 R |

Primary Examiner—Hezron E. Williams
Assistant Examiner—Craig Miller
Attorney, Agent, or Firm—Finnegan, Henderson, Farabow, Garrett and Dunner

[57] ABSTRACT

A device for measuring a gas dissolved in an oil comprising a sample container for containing a sample oil, an air bubble generator for extracting the gas dissolved in the oil, a gas container for containing the gas, a gas sensor for detecting the gas charged in the gas container, gas measuring means for measuring a concentration of the gas in response to a signal dispatched from the gas sensor, and a pump for supplying air to the air bubble generator.

20 Claims, 13 Drawing Sheets

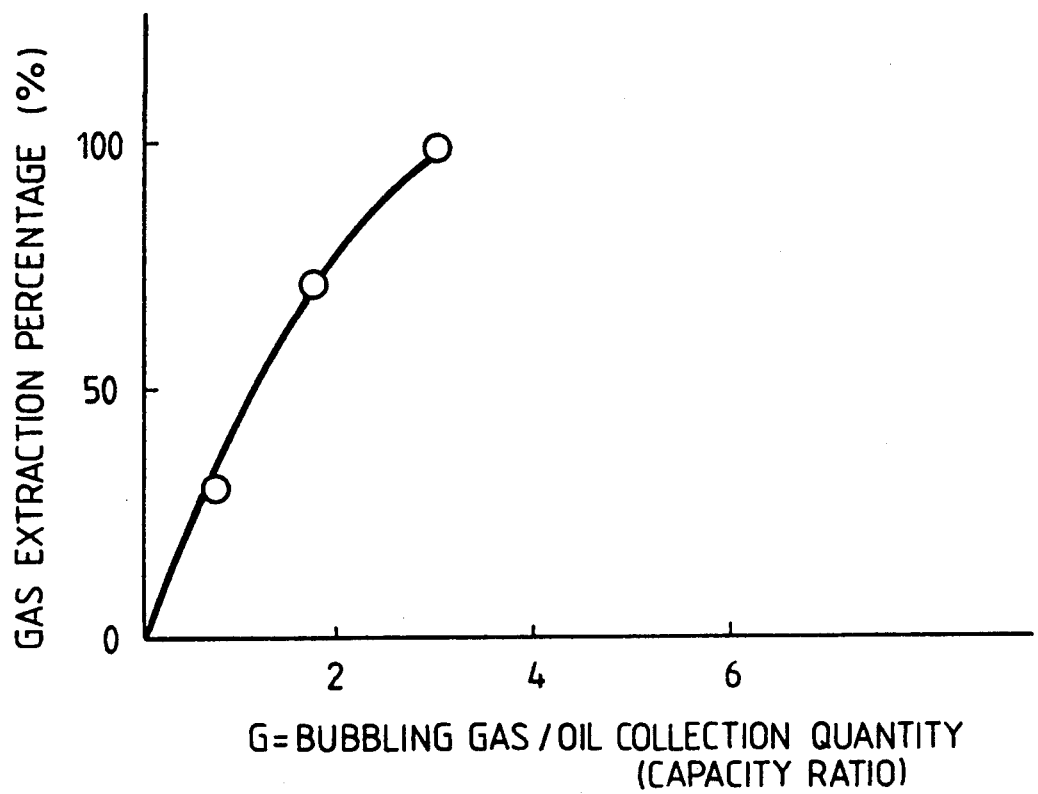

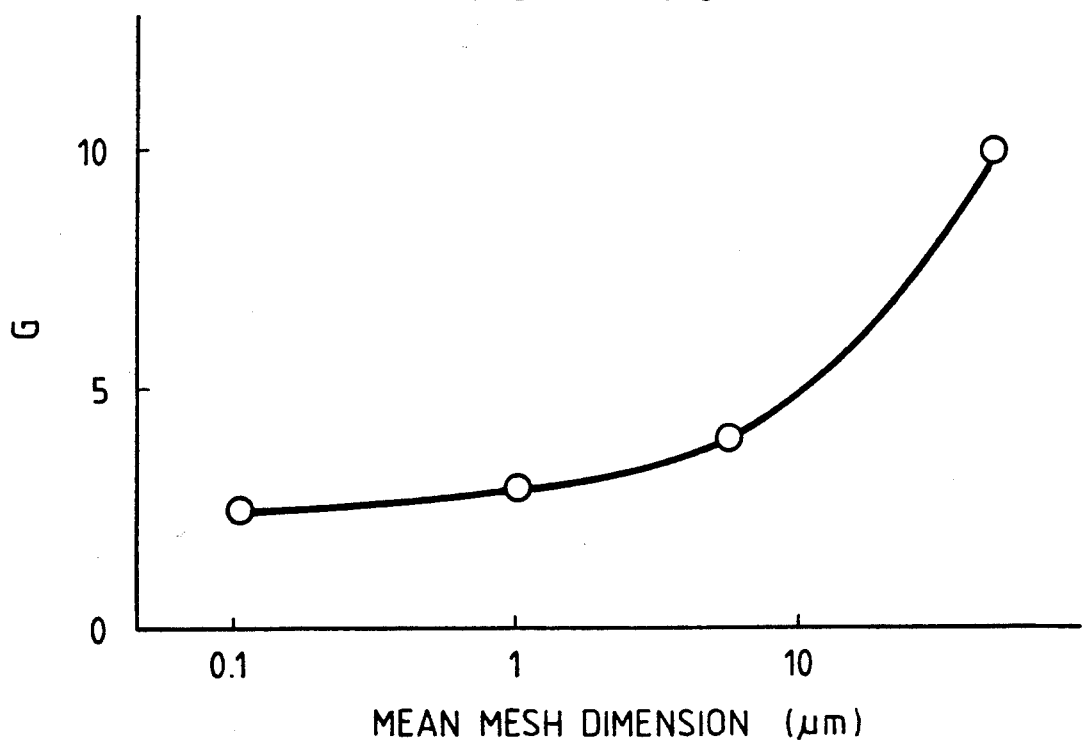

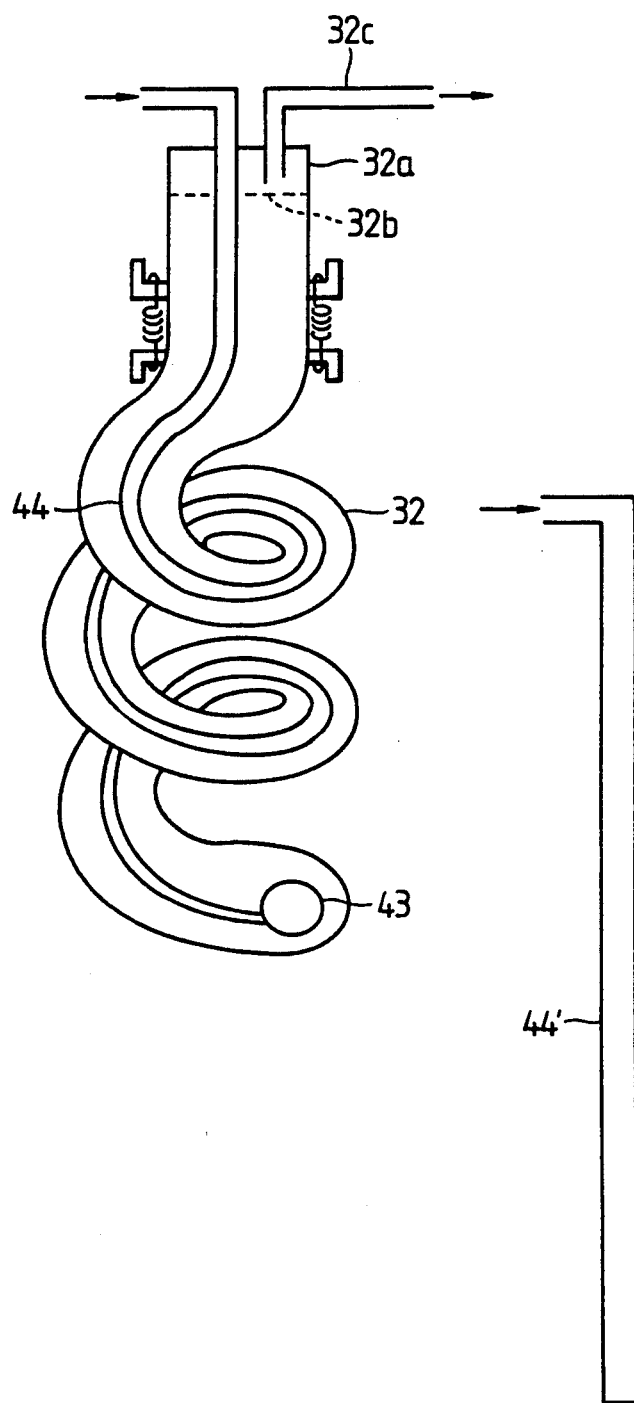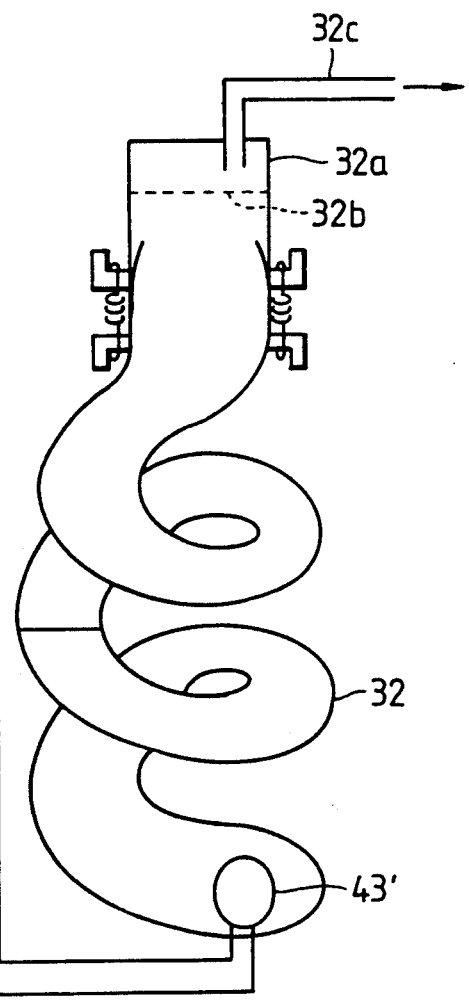

DEVICE FOR MEASURING GAS DISSOLVED IN OIL

This application is a continuation of application Ser. No. 231,296 filed Aug. 12, 1988 now abandoned.

BACKGROUND OF THE INVENTION

The present invention relates to an oil-dissolved-gas measuring device for measuring a concentration of a flammable gas dissolved in an insulating oil for use in an oil-immersed electrical appliance.

In oil-immersed electrical appliances such as a transformer, a capacitor, a reactor and so on, it is a well-known fact that an insulating oil and a solid insulating matter are decomposed with local heat or due to an abnormal state where corona discharge locally takes place, thereby evolving a flammable gas. It is therefore possible to detect the abnormality of the oil-immersed electrical appliance before encountering an accident by detecting the flammable gas.

According to the prior art, for maintenance of the oil-immersed electrical appliances there has heretofore been adopted a method of analyzing the gas dissolved in the insulating oil, i.e., the flammable gas such as hydrogen, methane and ethylene. In such a case, the insulating oil is sampled on the spot where the oil-immersed appliance is installed, and the sampled insulating oil (hereinafter referred to as "a sample oil") is brought back to a place at which an analyzer for analyzing the sample oil is disposed.

Prior to the analysis, the dissolved gas is extracted from the sample oil by Torricellian method, Toepler pump method or stripping method. The extracted dissolved gas is analyzed by a gas chromatography, and on the basis of the result of this analysis there is made a judgment as to whether the abnormal state appears or not. This is an example of the conventional method.

In the above-described conventional method, however, a good deal of time has to be spent until the analytic result is obtained through such processes as the sampling of sample oil, the extraction of dissolved gas and the analysis by the gas chromatography. Besides, an inert gas is required as a carrier gas because of employing the gas chromatography in such a method.

In addition, the apparatus for extracting the dissolved gas and the gas chromatography suited to analyze the gas employed in the above-mentioned method have large size and high cost.

SUMMARY OF THE INVENTION

It is an object of the present invention to provide a device for measuring a gas dissolved in an oil that is capable of quickly analyzing a dissolved gas on the spot where a sample oil is sampled.

To this end, according to one aspect of the invention, there is provided a device for measuring a gas dissolved in an oil comprising: a sample container for containing a sample oil; air bubble discharging means, provided in the sample container, for extracting a measurement gas dissolved in the sample oil; a gas container filled with the measurement gas extracted by the air bubble discharging means; gas detecting means for detecting the measurement gas charged in the gas container; measuring means for measuring a concentration of the measurement gas in response to a signal outputted by the gas detecting means, and pumping means for supplying air to the air bubble discharging means.

In accordance with the device for measuring a gas dissolved in an oil according to the present invention, the air bubbles are fed into the sample oil filled in the sample container by the air bubble discharging means, whereby the measurement gas dissolved in the sample oil is extracted. The thus extracted measurement gas is charged in the gas container. The gas detecting means outputs a signal corresponding to the concentration of the measurement gas. Based on the output signal, the measuring means measures the concentration of the measurement gas.

Hence, the operations ranging from the extraction of the dissolved gas from the sample oil to the measurement of concentration thereof can consecutively be performed by the single device. As a result, a short period of time suffices for the analysis of dissolved gas on the spot where the sample oil is sampled.

The above and other objects and advantages of the invention will become more apparent during the following discussion with reference to the accompanying drawings.

BRIEF DESCRIPTION OF THE DRAWINGS

FIG. 9 is a graphic chart showing gas extraction percentages of the dissolved gas with respect to a capacity ratio of an amount of bubbling gas to an amount of oil extraction;

FIG. 10 is a graphic chart showing a relation between the capacity ratio and a mean mesh dimension of a filter;

FIGS. 11 and 12 are views each illustrating modified forms of the air bubble generating means and the sample container which are shown in FIG. 8;

DETAILED DESCRIPTION OF THE PREFERRED EMBODIMENTS

The preferred embodiments of the present invention will be described hereinafter in greater detail. The present invention, however, is not limited to the following embodiments.

Figure 1:
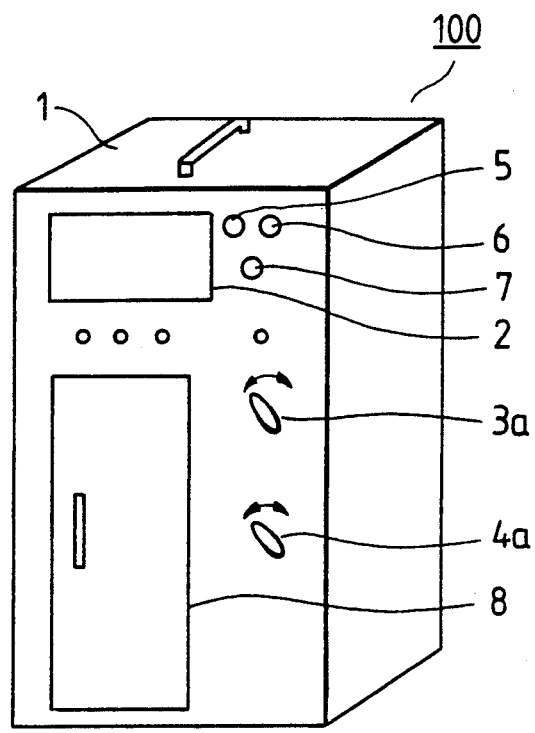
FIG. 1 is a perspective view of a first embodiment of a device for measuring a gas dissolved in an oil according to the present invention.

Referring first to FIG. 1, there is illustrated a perspective view of an oil-dissolved-gas measuring device 100 in a first embodiment of the present invention.

In FIG. 1, reference numeral 1 designates a case body on the front surface of which there are provided an analog meter 2 for indicating a concentration of a dissolved gas, operation levers 3a and 4a appropriate for a hexagonal valve 3 and a quadrangle valve 4 both designed for changing over a gas passageway, which will be explained in conjunction with FIG. 2; and knobs 5 to 7 for calibration of the meter 2. The numeral 8 denotes a door through which the sample oil is fed into a sample container 9. A capacity of the sample container 9 preferably ranges from 10 ml to 500 ml, and more preferably form 20 ml to 300 ml. The capacity may be fixed to a certain value or may be variable as the necessity arises.

Figure 2:
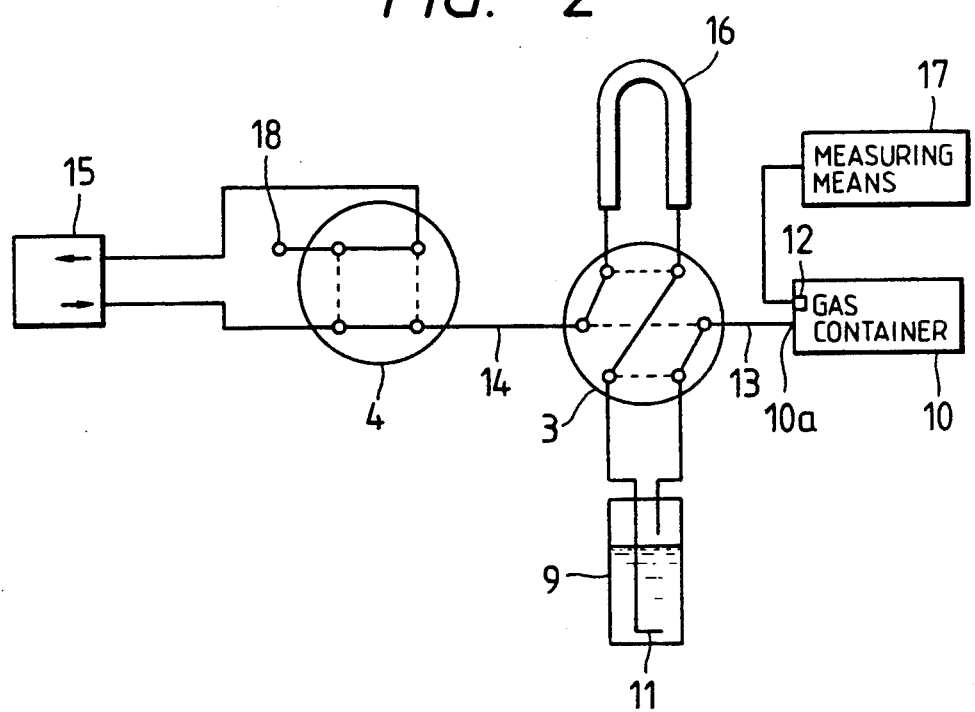
FIG. 2 is a schematic diagram illustrating operations of the measuring device depicted in FIG. 1.

FIG. 2 is a block diagram illustrating an internal construction of this embodiment.

In FIG. 2, a gas container 10 is preferably composed of, e.g., a tedler bag, a cylinder or a bellows-like tube (bellows) in which a predetermined capacity is obtained when being charged with the gas dissolved in the sample oil. The gas dissolved in the sample oil is extracted by air bubble discharging means (hereinafter referred to as a bubbler) incorporated in the glass or plastic sample container 9, this bubbler being formed of filter paper or a mesh metal net formed with fine holes which is hereinafter described. Namely, the capacity of the gas container 10 is almost 0 ml when being charged with no dissolved gas. While on the other hand, when the container is charged with the dissolved gas, its capacity is equivalent to a gas quantity necessary for measurement, e.g., about 100 ml to 2 l. This type of gas container suffices for use. Disposed inside the container in the vicinity of a dissolve gas inlet 10a of the gas container 10 is gas detecting means (hereinafter called a gas sensor) 12 which comprises, for instance, a semiconductor gas sensor. A connecting pipe 13 is connected to the dissolved gas inlet 10a, whereby the gas container is allowed to selectively communicate through the hexagonal valve 3 with the sample container 9. The hexagonal valve 3 is connected via a connecting pipe 14 to the quadrangle valve 4. In a state as depicted by a solid line in FIG. 2, there is formed a piping path through which the dissolved gas extracted by the bubbler 11 can be charged in the gas container 10. In a state as depicted by a broken line in FIG. 2, there is formed a piping path through which the gas filled in the gas container 10 can be discharged therefrom. The numeral 16 represents a dry column for drying the air fed from an air pump 15 which is used for extraction of the dissolved gas. The dry column 16 is filled with an adsorbent such as silicagel or zeolite. The adsorbent has a particle diameter of 1 mm or more enough to prevent a loss in pressure within the dry column 16. The numeral 17 represents measuring means connected to the gas sensor.

Figure 3:
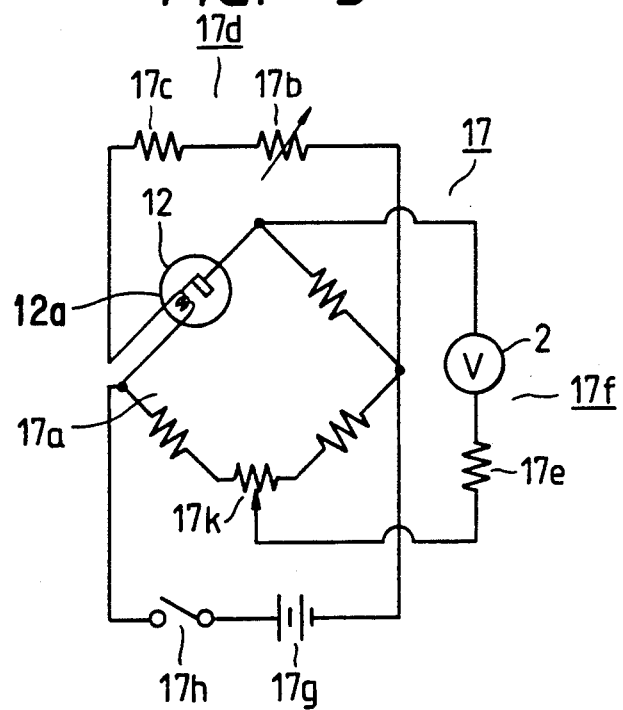
FIG. 3 is a diagram of an electric circuit of gas measuring means utilized in accordance with the present invention.

FIG. 3 is a diagram of an electric circuit of the measuring means 17. The electric circuit consists of a resistance bridge circuit 17a one side component of which is the gas sensor 12; a series circuit 17d comprising a variable resistor 17b for adjusting an amount of electricity with which a heater 12a of the gas sensor 12 is charged and a resistance 17c; a series circuit 17f comprising the meter 2 and a resistance 17e; a power source 17g; and a switch 17h. The resistance bridge circuit 17a has further a variable resistor 17k used for zero-adjustment of the meter 2.

Figure 4:
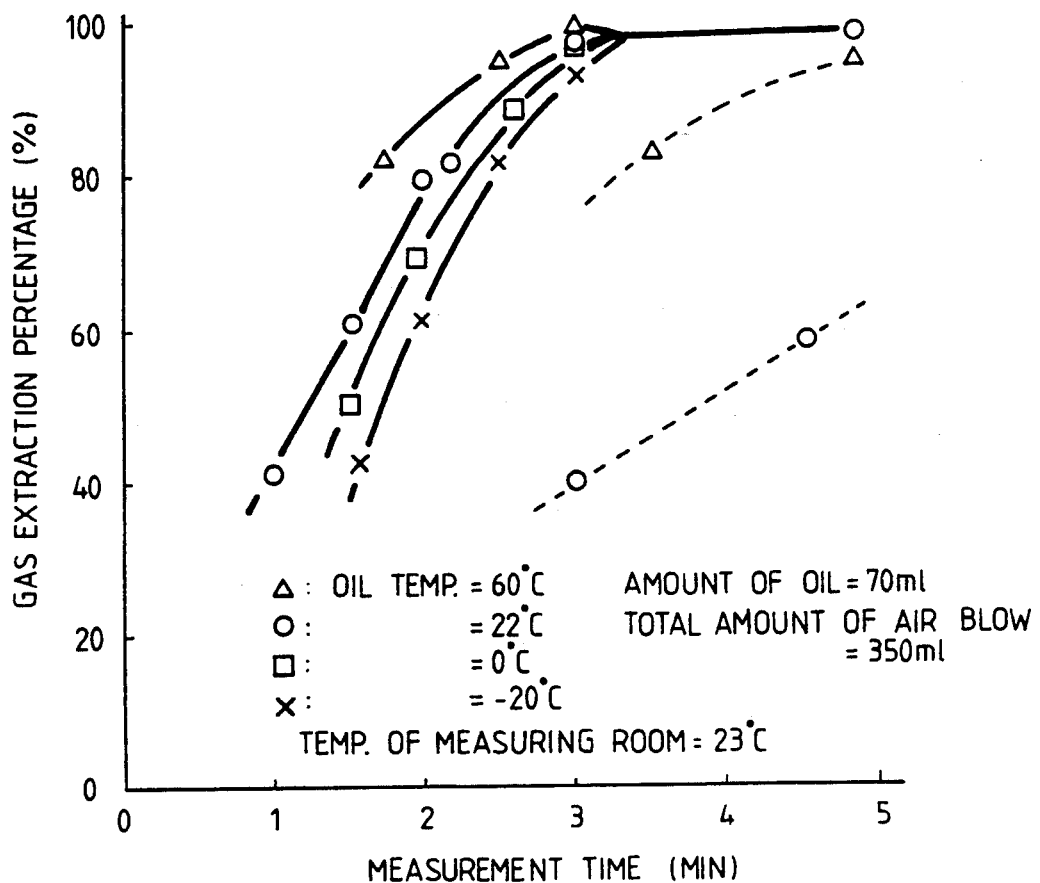
FIG. 4 is a graphic chart showing gas extraction percentages of the dissolved gas with respect to measurement time using diameter of air bubbles as a parameter.
Figure 5:
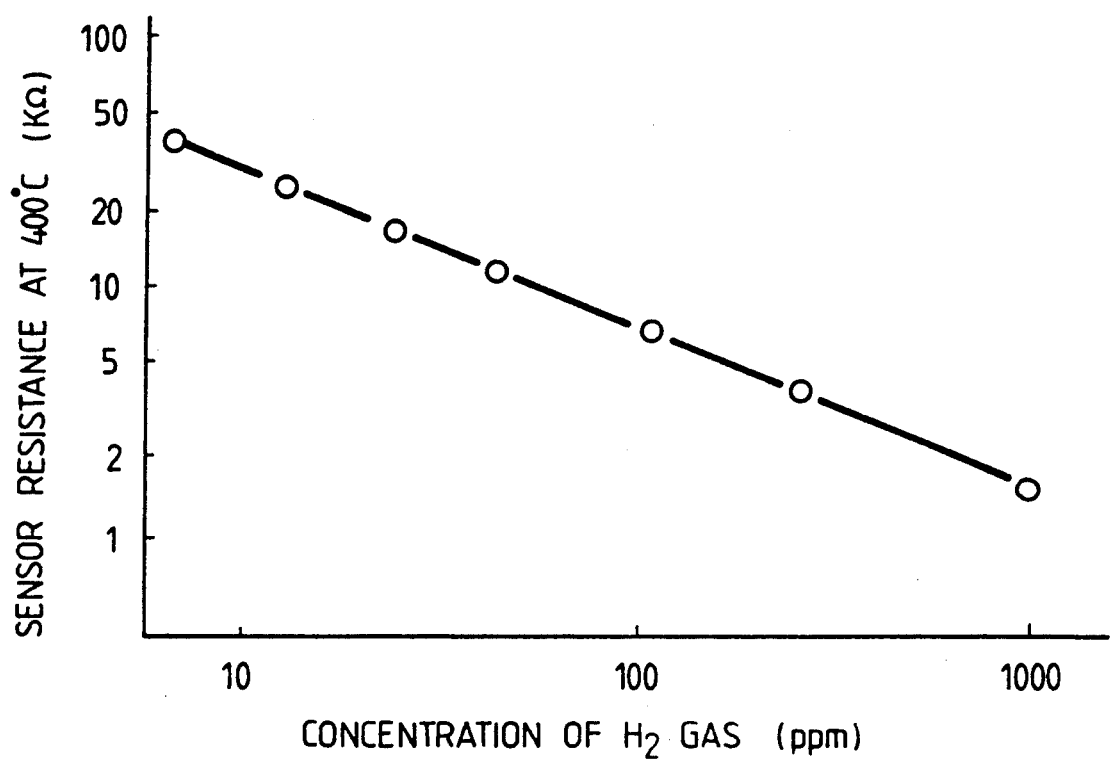
FIG. 5 is a characteristic diagram of a gas sensor.

The next description will be focused on the operations of this embodiment in conjunction with FIGS. 4 and 5.

In advance of the extraction of dissolved gas the gas container 10 is vacuumized (evacuated). The vacuumizing process is effected by actuating the air pump after the hexagonal valve 3 and the quadrangle valve 4 have come into the state as depicted by the broken line in FIG. 2.

Upon completion of the evacuation, the sample oil sampled from an oil-immersed electrical appliance defined as an object for maintenance is supplied into the sample container 9. Immediately after supplying the sample oil, the hexagonal valve 3 and the quadrangle valve 4 are changed over to the state as depicted by the solid line in FIG. 2, thereby actuating the air pump 15. In consequence of this, the air is fed from the air pump 15 via the quadrangle valve 4, the hexagonal valve 3 and the dry column 16 to the bubbler 11 where the bubbling is initiated. The dissolved gas in the sample oil is extracted together with the air by bubbling. The dissolved gas is charged in the gas container 10 through the hexagonal valve 3. When the gas container 10 is filled with the dissolved gas, although not illustrated, the air pump 15 is turned OFF by a pressure switch actuated when, for instance, the capacity of the gas container 10 reaches a predetermined value as described hereinafter, thus completing the extraction of dissolved gas. The time required for the extraction is approximately 1 to 2 minutes.

The measurement of a dissolved gas concentration can be initiated simultaneously when the gas container 10 is charged with the dissolved gas, because the gas sensor 12 is installed in the gas container 10. That is, the gas sensor 12 serves to detect the dissolved gas, and the meter 2 indicates the dissolved gas concentration when the equilibrium of the resistance bridge circuit 17a is lost.

In the above-described construction, a factor of extraction of the dissolved gas depends on a temperature of the sample oil, and hence it is preferable that the sample oil be used for the extraction of dissolved gas in a state in which the sample oil is heated to 40° C. or more. Turning attention to FIG. 4, FIG. 4 is a graph showing $H_2$ gas extraction percentages with respect to measurement time in a case where amounts of oil extracting and air blow are set to constant values (70 ml and 350 ml, respectively) and diameter of air bubbles is changed.

As is apparent from FIG. 4, as the diameter of the air bubbles is larger, the gas extraction percentage is more decreased. Particularly, the above characteristic is more remarkable as the temperature is decreased. Further, in a case where the air bubbles have diameters of 0.5 $\mu$m to 10 $\mu$m, the gas extraction percentage has a high value. For example, approximately 100% $H_2$ gas extraction is obtained at the measurement time of 3 minutes. Even if the oil temperature is decreased, the gas extraction percentage is still high. It is apparent from the result as shown in FIG. 4 that the diameter of the air bubbles has a great influence on the $H_2$ gas extraction efficiency and is required to be below 10 $\mu$m. A diameter of each of the bubbles produced by the bubbling can be diminished by decreasing the mesh dimension. If the time required for the passage of the bubbles through the sample oil is increased, an efficiency of extraction of the dissolved gas can be improved. Therefore, if the mesh dimension is reduced, the oil temperature is not necessarily increased. The amount of air blow is preferably 20 to 1000 ml/min., and more preferably 20 to 500 ml/min.

FIG. 5 is a graph showing characteristics of the gas sensor 9. In the case of, e.g., a hydrogen gas ($H_2$) selectivity sensor, a sensor resistance value is decreased so that this resistance value is substantially inversely proportional to a concentration of hydrogen gas. A relation between the gas concentration and the sensor resistance value is almost the same with methane and ethylene including hydrogen, if a commonly used flammable gas sensor is employed.

Based on the above-described manner, the measurement of concentration of the dissolved gas in one sample oil is terminated. Subsequently, the hexagonal valve 3 and the quandrangle valve 4 are, as illustrated in FIG. 2, changed over again to the state as depicted by the broken line, thereby discharging the gas in the gas container 10 preparatory to the next measurement. At this time, a discharge condition can be grasped from the fact that the indication of the meter 2 gradually goes down.

Where calibration of the measuring means 17 is effected prior to the measurement of the dissolved gas concentration, the gas having an already-known concentration may be sucked from suction port 18 leading to the quadrangle valve 4.

The detection concerning the completion of charging of the dissolved gas into the gas container may be performed by use of a switch like a microswitch which is operated in accordance with deformation of an outer wall of the gas container when the capacity of the gas container reaches a given value. As a gas sensor, a heat conductivity detector, a contact combustion type detector or a photo-sensor for sensing variations in color may be employed.

Figure 6:
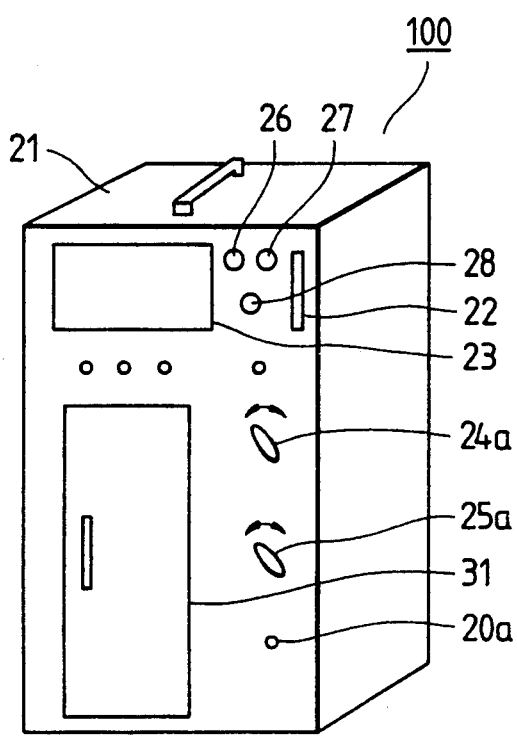
FIG. 6 is perspective view illustrating a second embodiment of the oil-dissolved-gas measuring device according to the present invention.

FIG. 6 shows a second embodiment of the device for measuring a gas dissolved in an oil according to the present invention. In the first embodiment the gas detecting means is provided in the gas container. In the second embodiment, however, the gas detecting means is disposed outside the gas container and is provided with a flowmeter for indicating a flow rate of air which is used for the extraction of dissolved gas.

In FIG. 6, a case body 21 includes a flowmeter 22, mounted on its front surface thereof, for indicating a flow rate of air which is used for the extraction of dissolved gas; an analog meter 23 for indicating a concentration of dissolved gas; levers 24a and 25a for operating hexagonal valves 24 and 25 for changing over a gas passageway which will be described in connection with FIG. 7; knobs 26 to 28 for calibration of a meter 23; and an operating member 20a of a cross valve 20 for changing over the passageway when effecting the calibration of gas detecting means 29 (hereinafter referred to as a gas sensor). The numeral 31 denotes a door for admitting the sample oil into a sample container 32.

Figure 7:
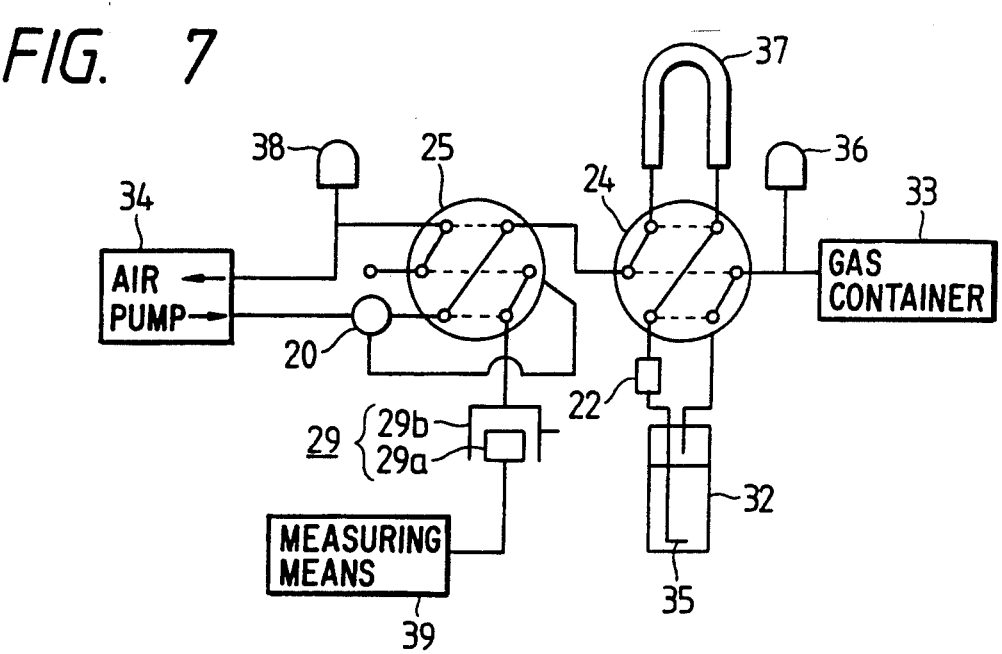
FIG. 7 is a schematic diagram showing the operations of the measuring device depicted in FIG. 6.

FIG. 7 is a block diagram illustrating an internal construction of the second embodiment.

In FIG. 7, a gas container 33 communicates with an air pump 34 alone by changing over two pieces of hexagonal valves 24 and 25 or with air bubble discharging means (a bubbler) 35 provided in the sample container, the gas sensor 29 and the air pump 34, respectively. A capacity of the gas container 33 is preferably 100 ml to 2 l, while a capacity of the sample container 32 is preferably 20 ml to 500 ml. This capacity may be fixed to a certain value or may be variable as the necessity arises.

An electric circuit of the measuring means 39 of this embodiment has the same arrangement as that in the first embodiment, and the description is therefore omitted herein.

Next, the operations of the second embodiment will be explained.

To start with, the gas container is vacuumized (evacuated) in advance of extracting the dissolved gas. This extraction is carried out by actuating the air pump 34 after the hexagonal valves 24 and 25, as illustrated in FIG. 7, have been brought into a state as shown by a broken line in the Figure. After the gas container 33 has been vacuumized, a vacuum switch 38 is operated. The vacuumizing process is completed by turning OFF the air pump 34.

In the wake of this step, the sample oil sampled from an oil-immersed electrical appliance defined as an object for maintenance is poured into the sample container 32. After the sample oil has been poured thereinto, the hexagonal valves 24 and 25 are changed over to the state as depicted by the solid line in FIG. 7. Then the air pump 34 is operated. Subsequently, the air is fed from the air pump 34 via the cross valve 20, the hexagonal valves 24 and 25, the dry column 37 and the flowmeter 22 to the bubbler 35, at which place the bubbling is initiated. The dissolved gas in the sample oil is extracted together with the air with the bubbling, and is further charged in the gas container 33 through the hexagonal valve 24. When the gas container 33 is filled with the dissolved gas, the pressure switch 36 is operated, whereby the air pump 34 is turned OFF. The extraction of dissolved gas is thus completed. The time necessary for extracting the dissolved gas is approximately 1 to 2 min.

Upon completion of the extraction of dissolved gas, the hexagonal valves 24 and 25 are changed over to the state as illustrated by the broken line in FIG. 7, and a concentration of dissolved gas is then measured. The dissolved gas filled in the gas container 33 is fed via the hexagonal valves 24 and 25, the air pump 34 and the cross valve 20 to the gas sensor 29 by actuating the air pump 34. Then, the gas sensor 29 detects the dissolved gas. The meter 23 indicates a concentration of dissolved gas when the equilibrium of the resistance bridge circuit 17a (FIG. 3) is lost.

The numeral 36 represents a pressure switch intended to turn OFF the air pump 34 when the dissolved gas charged (collected) in the gas container 33 reaches a predetermined quantity. The numeral 37 designates a dry column for drying the air fed from the air pump which is used for extracting the dissolved gas. The numeral 38 denotes a vacuum switch designed for turning OFF the air pump 34 when the gas container 33 is vacuumized. Measuring means 39 is connected to a sensor unit 29a of the gas sensor 29. The gas sensor 29 is composed of the sensor unit 29a and a sensor adaptor 29b accommodating the sensor unit 29a.

Figure 8:
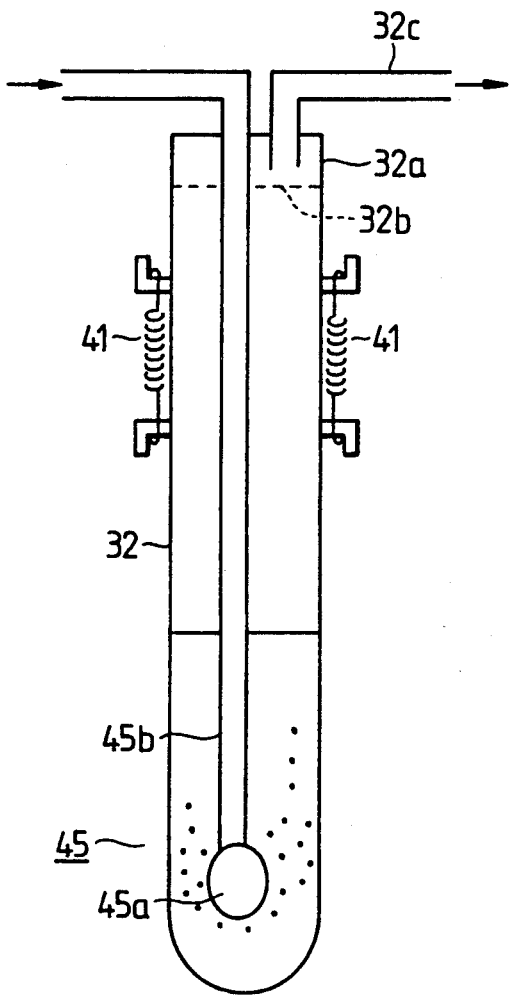
FIG. 8 is a cross-sectional view showing one embodiment of air bubble generating means and a sample container utilized in the present invention.

The bubblers (11 and 35) utilized in the first and second embodiments may be formed of such materials provided with fine holes as a gas filter, filter paper or a mesh metal net as to assume an arbitrary configuration. It is, however, preferable to adopt the bubbler as depicted in FIG. 8. This type of bubbler is constituted by a mesh filter 45a, having a mesh of 0.5 to 10 μm square, which is formed into a hollow spherical shape and also serves as a discharge portion of the air for the gas extraction, and a tube member 45b for leading the gas extraction air to the filter 45a. The tube member 45b is fixed to a cover 32a of the sample container 32 so that the filter 45a is positioned to reach almost the bottom of the sample container 32. The bubbler is thus provided in the sample container 32. The filter 45a is formed preferably of glass, filter paper or a metal net. A material of which the tube member 45b is formed is preferably glass or plastic.

The cover 32a of the sample container 32 is provided with a bubble eliminating net 32b for crushing (eliminating) the air bubbles produced from the sample oil. Fixed to a portion above the cover 32a is a tube member 32c for leading the extracted measurement gas to outside of the sample container 32. An inner peripheral surface of the cover 32a rubs against an outer peripheral surface of the upper portion of the sample container 32, thus sealing the sample container 32. The cover 32a is also biased downwards by dint of a coil spring 41.

In the above-described constitution, the bubbler 45 includes the mesh filter 45a having a mesh of 0.5 to 10 $\mu$m square, and hence a diameter of each of the bubbles produced by the bubbling is small. As a result, the time (hereinafter referred to as a residence time) for which the bubbles pass through the sample oil increases. Namely, a volume of the bubble becomes small, as the bubble diameter decreases. Hence, buoyancy received from the sample oil decreases, while the residence time is lengthened. If the residence time of the bubbles increases, the amount of dissolved gas taken in the air bubbles augment, thereby improving a factor of the extraction of dissolved gas (a bubbling recovery percentage).

Let the air bubble diameter be r, and the extraction quantity of dissolved gas is obtained as follows.

Assuming the volume of the bubble is Vo (cm$^3$), the surface area thereof is So (cm$^2$), the air passage quantity per minute is V (cm$^3$/min.), the number of bubbles per minute is N, and the total surface area of the bubble per minute is S (cm$^2$), the following equations are established:

$$Vo = \frac{4}{3}\pi r^3 \quad (1)$$

$$So = 4\pi r^2 \quad (2)$$

$$N = \frac{V}{vo} \quad (3)$$

$$S = So \cdot N \quad (4)$$
$$= \frac{4\pi r^2 \cdot V}{\frac{4}{3}\pi r^3} = \frac{3V}{r}$$

Next, assuming the residence time of the bubbles is t (min.), the coefficient of diffusion of the dissolved gas is a (cm$^3$/cm$^2$·min.), and the take-in quantity $V_G$ (cm$^3$) with which one bubble is capable of taking therein the dissolved gas for the time t is expressed as follows:

$$V_G = a \cdot So \cdot t \ldots \quad (5)$$

Then, assuming the air blow time is T (min.) and the total take-in quantity VG with which all of the bubbles are capable of containing the dissolved gas is by:

$$V_G = v_G \cdot N \cdot T \quad (6)$$
$$= a \cdot 4\pi r^2 \cdot t \cdot \frac{V}{\frac{4}{3}\pi r^3} \cdot T$$
$$= 3aVT \cdot \frac{t}{r}$$

In the formula (6), if 3aVT = k (constant), it can be found that the extraction quantity of dissolved gas is increased by lengthening the residence time of the bubbles or reducing a diameter of air bubble. Therefore, the extraction quantity can be increased, as the mesh of the filter 45a of the bubbler 45 becomes small. Taking the loading into consideration, the excellent properties can be exhibited, if the mesh is not less than 0.5 $\mu$m square but not more than 10 $\mu$m square in terms of the gas extraction percentage.

FIG. 9 is a graph showing gas extraction percentages of the dissolved gas with respect to a capacity ratio of an amount of bubbling gas to an amount of extraction of oil. If there are prepared the bubbling gas quantity that is three times as large as the extracted oil quantity, a gas extraction percentage of almost 100% can be obtained. Provided that H$_2$ gas of, e.g., 100 ppm is dissolved in the sample oil, and if 100% gas extraction is to be attained, H$_2$ gas of 33 ppm exists in the air extracted by the bubbling. Hence, H$_2$ gas can sufficiently be detected by a gas sensor capable of detecting such a value as 33 ppm. The bubbling gas quantity is preferably is 50 to 1000 ml/min..

FIG. 10 is a graph showing a relation between the capacity ratio and a mean mesh dimension of the filter 45a. It can be understood from FIG. 10 that the mean mesh dimension may be approximately 10 $\mu$m square to obtain a capacity ratio 3, viz., a extraction percentage of 100%.

FIGS. 11 and 12 illustrate other embodiments of the bubbler 45, wherein the sample container is arranged to be a spiral tube in order to increase the residence time of the bubbles. In the embodiment shown in FIG. 11, as in the case of the sample container 32, a tube member 44 for feeding the air to the filter 43 is similarly arranged to be a helical tube provided in the sample container 32. In the embodiment shown in FIG. 12, only the filter 43' is disposed in the sample container 32, while the tube member 44' is fixedly provided outside the sample container 32. The tube member 44' is led from the bottom of the sample container 32 to the inside thereof and is further connected to the filter 43'.

For the purpose of increasing the residence time of the bubbles, the sample oil may be stirred at a low velocity during the bubbling, with the result that the air bubbles rise up helically in the sample oil.

In general, the air bubbles produced in the sample container by the bubble generating means are hard to disappear, and the residual bubbles are led through the pipe to the gas container and further to the gas detector. Consequently, adverse influences are probably exerted on the gas detection. For this reason, in some cases the amount of air supplied from the air pump for the extraction of dissolved gas has to be diminished, or the diameter of air bubble has to be enlarged by the air bubble generating means, resulting in a considerable increment in the time required for extracting the gas. To obviate this defect, there may be provided air bubble eliminating means such as an air bubble eliminating net (32b) as depicted in FIG. 8, for eliminating the air bubbles generated in the sample container.

Figure 13:
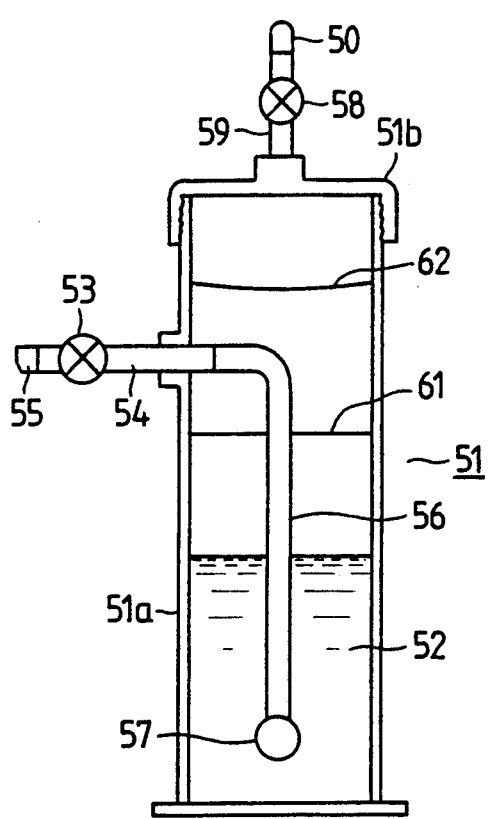
FIG. 13 is a view illustrating the sample container provided with air bubble eliminating means.

FIG. 13 illustrates one embodiment of the sample container provided with the bubble eliminating means, and FIG. 14 is a front elevation showing one embodiment of the air bubble eliminating means.

In the Figures, the numeral 51 represents a cylindrical sample container, formed of plastic resin, into which a sample oil 52 is poured. The sample container 51 is composed of a body unit 51a for reserving the sample oil 52 and a cover member 51b which is to be removed when pouring the sample oil thereinto. Air-tightly fitted to the body unit 51b is a pipe 54 mounted with a valve 53, passing through the side wall thereof. One end of the pipe 54 is connected to a flexible tube 55 for leading the gas extraction air fed from an unillustrated air pump, while the other end thereof is connected to an L-shaped air introducing pipe 56 formed of glass or plastic resin. The tip of this L-shaped air introducing pipe 56 is arranged to substantially reach the bottom of the body unit 51a and is also fitted with a filter 57 formed of glass fiber or the like, thus functioning as the air bubble generating means.

Figure 14A:
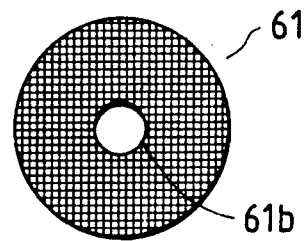
FIG. 14 is a view illustrating one embodiment of the air bubble eliminating means.
Figure 14B:
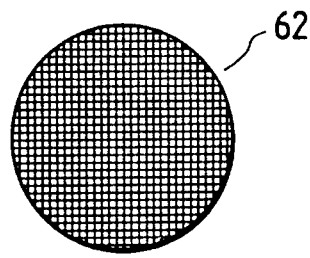

On the other hand, as in the previous case a pipe 59 mounted with a valve 58 is airtightly attached to the cover member 51b, penetrating the wall thereof. The pipe 59 is connected to a flexible tube 50 for leading the extracted gas in the sample container 51 to the unillustrated gas container. The numerals 61 and 62 represent nets intended to eliminate the air bubbles. The nets 61 and 62 are disposed in such positions that they do not contact the sample oil 52 when pouring the sample oil 52 into the sample container 51, i.e., these nets are provided in an air space in the sample container 51. The net 61 is, as illustrated in FIG. 14(a), formed in such a way that the central portion thereof is hollowed in a doughnut-like configuration to adapt itself to the diameter of the L-shaped air introducing pipe 56 and a notch 61a is formed in a portion thereof. The net 61 is bonded to the L-shaped air introducing pipe 56 with, e.g., a bonding agent. The net 62 is, as depicted in FIG. 14(b), cut out to have a diameter slightly larger than an inside diameter of the body unit 51a of the sample container 51. Then, the net 62 is fitted therein along a side wall of the body unit 51a. The nets 61 and 62 cooperate to function as the air bubble eliminating means for eliminating the produced air bubbles.

Next, an experimental example will be explained. The operation begins with selecting nets, as the nets 61 and 62, having a roughness of 16 meshes (1 mm square). These metal nets are, as shown in FIG. 13, set at two stages in the sample container (200 ml), and the sample oil (70 ml) is poured thereinto. Subsequent to this step, there are made some examinations by varying the amount of gas extraction air supplied from the air pump.

It is noted that the filter to be used is the one having a hole diameter of 0.2 to 10 $\mu$m. Consequently, where the metal nets are provided, it has been confirmed that the air bubbles generated do not permeate in the pipe leading to the gas container, even when feeding the gas extraction air at a flow velocity of 120 ml/min. In contrast with this, in the case of providing no metal net, the air bubbles come in the pipe at a flow velocity of 90 ml/min. As is clarified from the above-described results, the provision of metal nets permits an increment in the amount of gas extraction air supply to the sample oil, thereby reducing the time needed for extracting the gas.

The gas container employed in the present invention involves the use of a resinous film bag. This resinous film bag, however, has some defects in which repetitive usage thereof conduces to variations in recovery capacity because of expansion of film and further to easy breakdown thereof, and the durability is relatively low.

In order to solve these problems, it is proposed that the gas container is formed of a rubber bag, and this rubber bag is encased by a hard case for regulating the expansion of bag, which exceeds a predetermined amount, by forcing down it from outside. The description will further be given in conjunction with FIGS. 15 and 16 by exemplifying a case where this concrete structure is applied to the first embodiment (the gas sensor is installed in the gas container).

The numeral 71 designates a sample container filled with an insulating oil 72 taken from a transformer or the like, for extracting the gas by bubbling. A bubbler 74 into which the air is fed from a pump 73 is provided in the sample container 71. The bubbling is effected by the air bubbles generated by the bubbler 74, whereby a gas existing in the insulating oil, e.g., hydrogen gas, is taken together with the air bubbles from a pipe 75.

A rubber bag 76 is formed of, for instance, natural rubber butyl rubber, chloroprene rubber, nitrile butadiene rubber and styrene butadiene rubber, the thickness of which is preferably about 2 mm or less. A hard case 77 suitable for use is formed of, for example, resin such as polyethylene, polypropylene and polyvinyl chloride or of an adequate metal.

The bag 76 is encased by the case 77, and an open end thereof is attached to an open end of the case 77. More specifically, a cover 79 is fitted through a packing 78 to the inner surface of the opening of the case 77. At this time, the open end of the bag 76 is sandwiched in between the packing 78 and the peripheral surface of the cover 79. The outer periphery of the opening of the case 77 is fastened with a hose band 70, whereby the bag 76 is fixedly installed in the case 77.

The numeral 81 represents a discharge port formed in a portion of the case 77. As will be mentioned later, when the bag expands, the air in the case 77 is discharged outside from the discharge port 81. A gas sensor 82 serves to measure a concentration of the gas collected in the bag 76 and is, as illustrated in the Figure, mounted on the inner surface of the cover 79. A pressure sensor 83 for measuring an internal pressure of the bag 76 is, as shown in the Figure, connected to a pipe 75.

Figure 15:
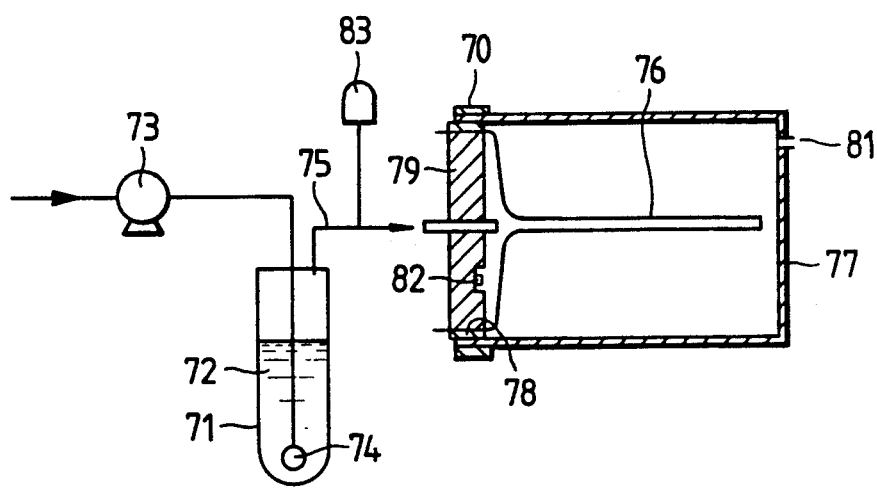
FIGS. 15 and 16 are views showing one embodiment of a gas container utilized in the present invention.
Figure 16:
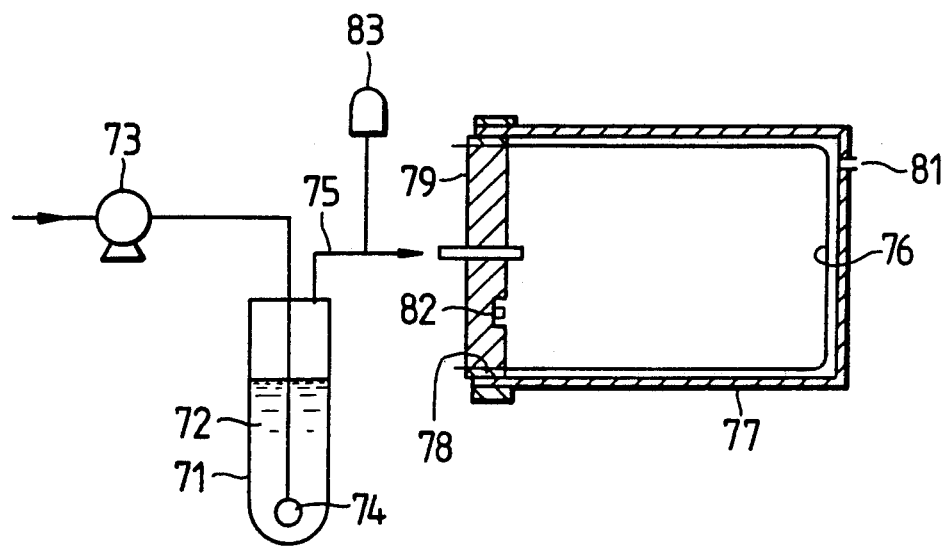

Referring now to FIG. 15, there is illustrated a state where the gas is not yet collected. Then, the gas is fed from the sample container 71 via the pipe 75 into the bag 76. As this feeding process advances, the bag is gradually swollen. When the outer periphery of the bag 76 is brought into contact with the inner surface of the case 77 due to the expansion thereof, the bag can not be swollen any more because of its being regulated by the case 77. Thus, a quantity of gas collected by the bag remains constant.

The internal pressure of the bag at that time is detected by the pressure sensor 83. Immediately after the pressure sensor 83 has detected the internal pressure, the operation of, e.g., the pump 73 is halted to cease the further bubbling, thus stopping the supply of gas into the bag 76. The gas sensor 82 measures the concentration of gas in the bag.

In second place, an experimental example in this embodiment will be explained. The bag 76 formed of the natural rubber and the case 77 formed of polyethylene are employed. The bag 76 is supplied with the air till reaching 0.08 kg/cm$^2$, and subsequently the air is discharged till reaching a degree of vacuum of 600 mmHg. The supply and discharge of are repeated. Even after 10000 repetitions have been carried out, no abnormality can be seen in the bag 76.

In the case of a bag formed of fluoride vinyl film, the supply and discharge of air are repeated under the same conditions. As a result of 200 repetitions, the bag is damaged. As is obvious from this experiment, the bag according to this embodiment has superior durability.

Figure 17:
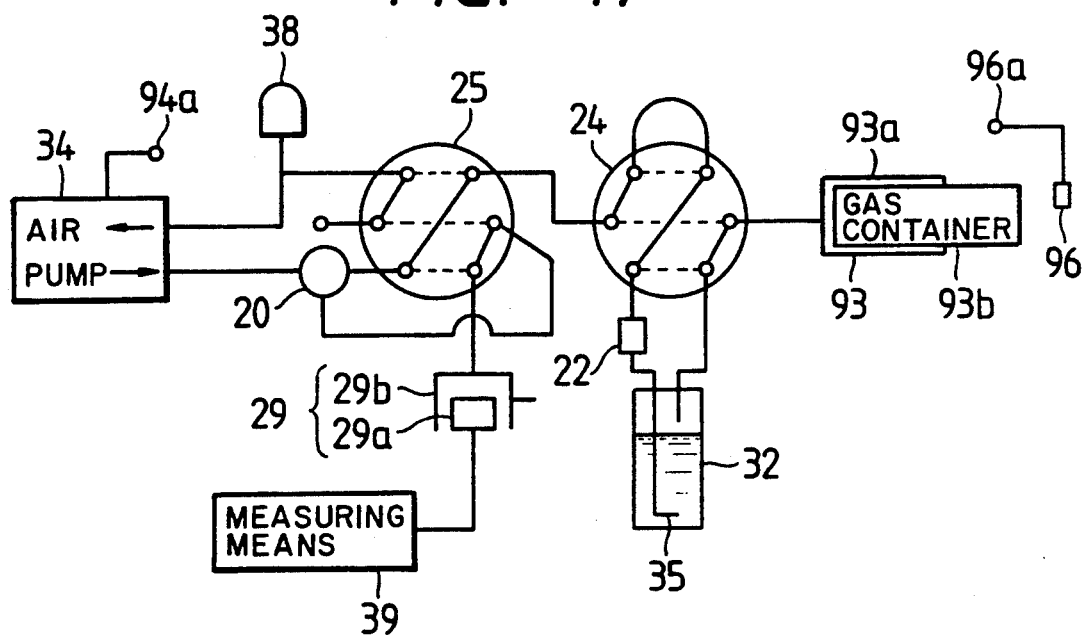
FIG. 17 is a diagram showing another embodiment of the gas container.

FIG. 17 is a schematic diagram shows another embodiment of the gas container. In FIG. 17, the numeral 93 represents a gas container the capacity of which is variable depending on a combination of a cylinder 93a and a piston 93b. Its maximum capacity is preferably about 50 ml to 1 l. In this case, the expansion and contraction of the container, which are concomitant with the pouring process of the dissolved gas into the gas container, do not take place. Hence, the above-mentioned problem is already solved. The numeral 96 denotes switch means (hereinafter called a limit switch). The limit switch 96 is disposed in such a position as to function when reaching the maximum capacity in a case where the gas container 93 is charged (collection) with the dissolved gas, viz., in such a position that the piston 93b moves with the maximum stroke within the cylinder 93a and impinges thereon. The limit switch 96 behaves to control energization of the air pump 34, i.e., turns OFF the pump 34. A terminal 94a of the air pump 34 is, although not illustrated, electrically connected to a terminal 96a of the limit switch 96. Other components are the same as those in the second embodiment of FIG. 7 according to the present invention, and the description is therefore omitted herein. Particularly, the switching operation of the switch means 96 will now be mentioned.

Because of the bubbling within the sample container, the dissolved gas in the sample oil is extracted together with the air and is then charged via the hexagonal valve 24 in the gas container 93. The dissolved gas is filled in the gas container 93, and the capacity of the gas container 93 is fully reached. Subsequently, the piston 93b moves and impinges on the limit switch 96, whereby the limit switch comes to function. The air pump 34 is turned OFF, thus completing the extraction of dissolved gas. The time required for the extraction is approximately 1 to 4 minutes.

Upon completion of the extraction of dissolved gas, the hexagonal valves 24 and 25 are changed over to a state as depicted with a broken line in FIG. 17, and a concentration of dissolved gas is measured. The dissolved gas charged in the gas container 93 is fed via the hexagonal valves 24 and 25, the air pump 34 and the cross valve 20 to the gas sensor 39 by actuating the air pump 34. Based on this arrangement, the gas sensor 39 detects the dissolved gas, and a meter 23 indicates the concentration of dissolved gas when the equilibrium of a resistance bridge circuit 29a is lost.

In the above-described embodiments, the gas container is connected through the pump and the valves to the gas detecting means. As in the first embodiment shown in FIG. 2, the gas detecting means may, as a matter of course, be provided in the gas container. Where such an arrangement is made, the valve operation can be facilitated, and the construction thereof can also be simplified.

The switch means may be a pressure switch disposed on the piping path to the gas container. In this case, if a gauge pressure is set to 0.01 to 1 kg/cm$^2$, as in the above-described embodiments, it is possible to readily make uniform the extraction quantity of dissolved gas. Supposing that this pressure switch can be used in cooperation with a depressurizing switch which works under a depressurization gauge pressure of $-0.05$ to $-0.5$ kg/cm$^2$, it is feasible to grasp a condition under which the gas container is evacuated. Hence, the operation of the air pump for discharge can also be controlled.

In the embodiments discussed above, the air for the bubbling is introduced via the air pump directly into the sample oil. On the other hand, the bubble generator like a ball filter used for generating the air bubbles produces minute air bubbles each having a diameter of approximately 5 to 10 $\mu$m at maximum. A surface area of air bubble increases, as the diameter thereof becomes small.

Figure 18:
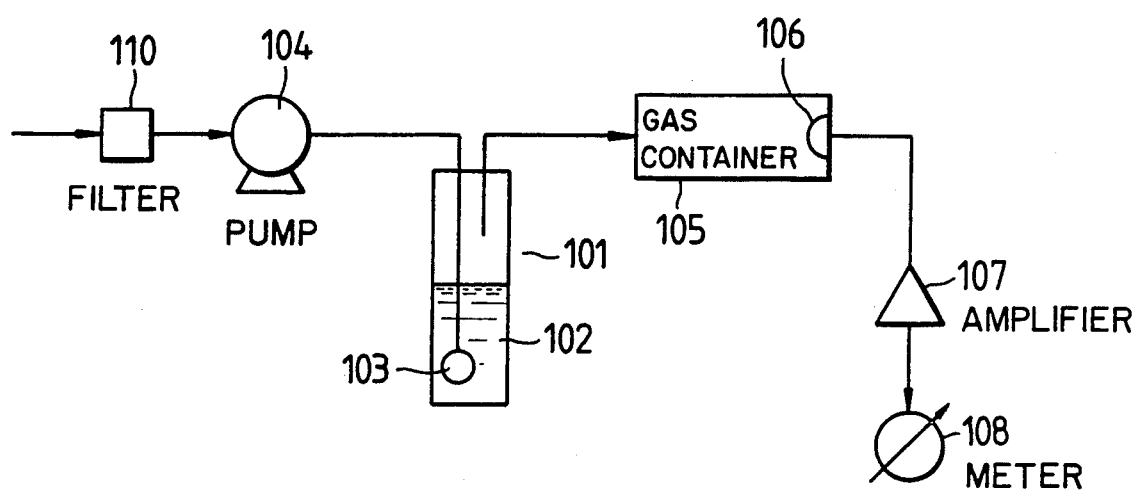
FIG. 18 is a schematic diagram illustrating the gas measuring device having a filter interposed between an air pump and the air bubble generating means.

As explained earlier, if the air is introduced directly into the sample oil, in some cases an efficiency of gas extraction based on the bubbling is declined during the use. The reason for this is, it can be considered, that: the bubble generator for performing the bubbling undergoes loading due to dust contained in the air; the fine air bubbles do not come out, instead only the bubbles having a large diameter are generated; and the sufficient surface area can not be ensured, thereby decreasing the efficiency of extraction. There is proposed a method of obviating such problems, wherein the bubbling gas is introduced via the filter to the bubble generator. This will be described with reference to FIG. 18.

A sample container 101 contains a sample oil 102 and incorporates a bubble generator 103 consisting of a ball filter. The bubble generator 103 is fed with a bubbling gas, e.g., the air from outside through a pump 104.

The air bubbles are produced in combination with the air. The gas dissolved in the sample oil 102 is contained in the air bubbles. The extracted gas is fed to a gas container 105, at which place the gas is detected by means of a gas sensor 106. A resultant detection value is converted into an electric signal and is amplified by an amplifier 107. Then, a detection quantity is indicated by the meter 108.

In accordance with this embodiment, the air for the bubbling is purified by a filter 110 and is transferred to a bubble generator 103. To be specific, the air passing through the filter 110 is sent to the pump 104, from which place the air is further fed to the bubble generator 103.

Figure 19:
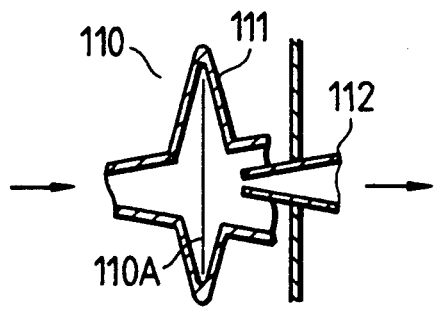
FIG. 19 is a view depicting a concrete structure of the filter.

FIG. 19 shows one example of the filter 110. The filter 110 includes an introduction passageway formed on the side of an inlet of a case 111, and a filter body 110A provided therein. The air passes through the filter body 110A, and the air is thereby purified.

Figure 20:
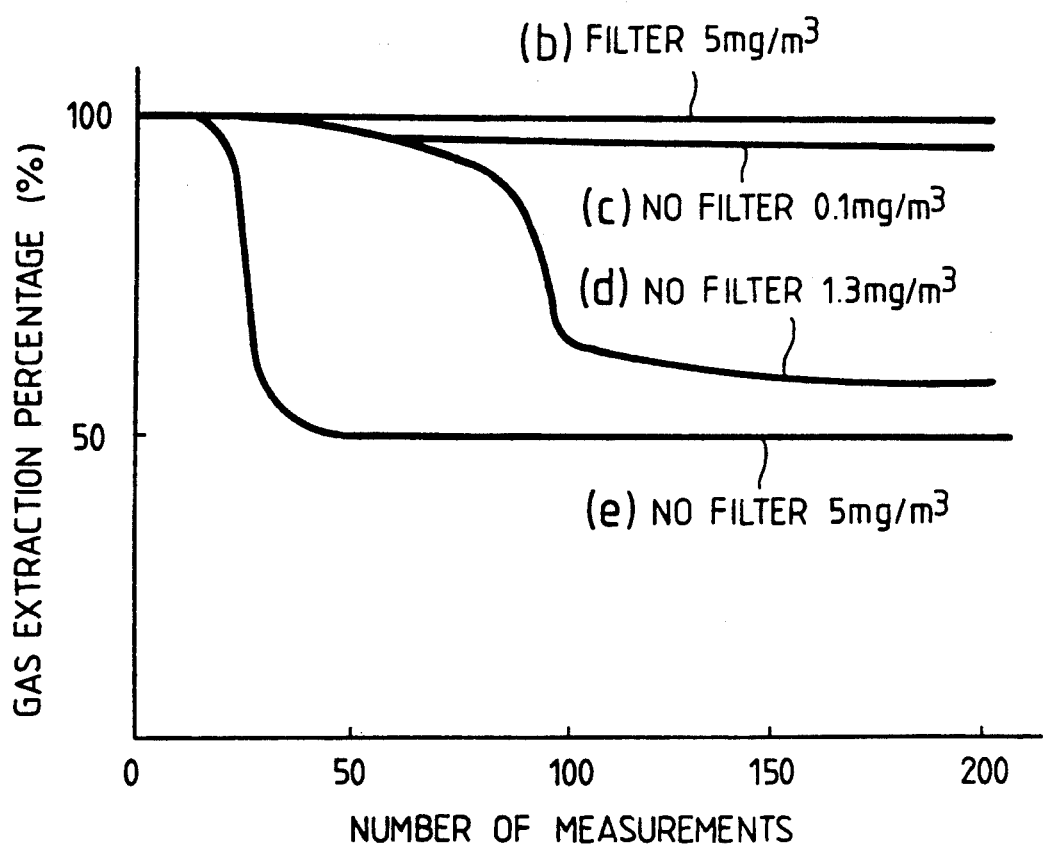
FIG. 20 is an experimental characteristic diagram showing the gas extraction percentages.

FIG. 20 shows results of an experiment performed by the present inventor. Since a diameter of each air bubble generated by the bubble generator 103 is 5 to 10 $\mu$m, an available filter 110 has a hole diameter of 0.5 $\mu$m or less, as a matter of fact, less than 0.2 $\mu$m. In FIG. 20, each of the numerical values marked with parentheses indicates a density of dust contained in the air fed by the pump 104.

As is obvious from FIG. 20, when a density of dust is small, a gas recovery percentage does not decrease so much, even if no filter 110 is employed. Where the concentration is high, however, the gas recovery percentage exhibits 50% or less until the number of measurements comes to 100. This is, it can be considered, attributed to the fact that the loading is created in the bubble generator because of the dust contained in the air, and the air bubbles having a predetermined hole diameter are not generated.

In contract with this, when making use of the air purified by its passing therethrough, even in the case of a high dust concentration, it is apparently feasible to keep the gas extraction percentaqe high for a long stretch of time. The loading proves to be effectively avoidable owing to the air purified by the filter 110. The air bubbles are thus produced in the sample oil, and the oil-dissolved gas, which is to be extracted in the above-mentioned manner, is collected into a gas container where the gas measurement is effected. At this time, it is possible to maintain the gas extraction percentage to a high value for a long period of time.

The present invention provides the following effects. The device itself can be compactly constructed, and hence it is possible to analyze the dissolved gas in a short time on the spot where the oil-immersed electrical appliance is installed. Besides, the oil-dissolved-gas measuring device capable of improving the operativity of gas analysis can be acquired. This compact construction permits a drop in cost of manufacture thereof. Because the gas sensor is employed more sensitive analysis than the gas chromatography is attained. Where the gas sensor is provided in the gas container, it is feasible to know a degree to which the gas which has undergone the complete measurement is discharged from the gas container with the aid of meter.

The air bubble discharging means uses the filter having a mesh of 0.5 to 10 $\mu$m square, so that it is possible to extract the dissolved gas with a high efficiency and a high concentration without causing a rise in temperature of the collected sample oil. Hence, the gas extraction quantity is small, the measurement time can be reduced, and further the accuracy can be enhanced.

The arrangement that the air bubble eliminating means is disposed within the sample container contributes to prevention of adverse influences caused by the air bubbles on the gas detection. Moreover, the container for collecting the gas on the basis of bubbling is constructed by encasing the rubber bag into the case, thereby exhibiting excellent durability. This further permits the constant collection of a specified amount of gas. It can therefore be expected that the accurate gas measurement is to be carried out. Since the bubbling gas is fed via the filter to the bubble generating means, the loading in the bubble generator can be avoided on the occasion of extracting the gas dissolved in the oil on the basis of bubbling. As a result, the high gas extraction percentage can be maintained for a long time.

Although the illustrative embodiments of the present invention have been described in greater detail with reference to the accompanying drawings, it is to be understood that the invention is not limited to those precise embodiments. Various changes or modifications may be effected therein by one skilled in the art without departing from the scope or the spirit of the invention.

What is claimed is:

1. A device for measuring a gas dissolved in an oil sample, comprising:
   a sample container for containing an oil sample;
   an air bubble discharging means, provided in said sample container, for extracting a measurement gas dissolved in said oil sample;
   a gas container for containing said measurement gas extracted by said air bubble discharging means;
   gas detecting means for detecting said measurement gas charged in said gas container;
   measuring means for measuring a concentration of said measurement gas in response to a signal dispatched from said gas detecting means;
   pumping means for supplying air to said air bubble discharging means; and
   filter means for purifying the air before being fed into said air bubble dischrging means;
   said air bubble discharging means comprising a mesh filter having a mesh of 0.5 to 10 $\mu$m square for discharging bubbles therefrom and air leading means for leading air to said discharging means.

2. A device as claimed in claim 1, wherein said sample container comprises a housing for containing the sample oil and at least said discharging means of said air bubble discharging means, said housing having at least one opening for passing a bubble air and a gas dissolved in said sample oil.

3. A device for measuring a gas dissolved in an oil sample, comprising:
   a sample container for containing an oil sample;
   an air bubble discharging means, provided in said sample container, for extracting a measurement gas dissolved in said oil sample;
   a gas container for containing said measurement gas extracted by said air bubble discharging means;
   gas detecting means for detecting said measurement gas charged in said gas container;
   measuring means for measuring a concentration of said measurement gas in response to a signal dispatched from said gas detecting means;
   pumping means for supplying air to said air bubble discharging means; and
   filter means for purifying the air before being fed into said air bubble dischrging means;
   said air bubble discharging means comprising a mesh filter having a mesh of 0.5 to 10 $\mu$m square for discharging bubbles therefrom and air leading means for leading air to said discharging means;
   wherein said sample container is in a spiral form.

4. A device as claimed in claim 3, wherein said air leading means is contained in said housing and is in the spiral form.

5. A device for measuring a gas dissolved in an oil sample, comprising:
   a sample container for containing an oil sample;
   an air bubble discharging means, provided in said sample container, for extracting a measurement gas dissolved in said oil sample;
   a gas container for containing said measurement gas extracted by said air bubble discharging means;
   gas detecting means for detecting said measurement gas charged in said gas container;
   measuring means for measuring a concentration of said measurement gas in response to a signal dispatched from said gas detecting means;
   pumping means for supplying air to said air bubble discharging means; and
   filter means for purifying the air before being fed into said air bubble discharging means;
   said air bubble discharging means comprising a mesh filter having a mesh of 0.5 to 10 $\mu$m square for discharging bubbles therefrom and air leading means for leading air to said discharging means;

said device further comprising gas-passage switching means for selecting one of first and second passages according to gas detecting operation and gas discharging operation, respectively, said first passage communicating said pumping means through said air bubble discharging means to said gas container and said second passage communicating said gas container to said pumping means.

6. A device as claimed in claim 5, further including air drying means in said first passage for drying the air from said pumping means, wherein said air drying means comprises a dry column filled with an absorbent material comprising any one of silica gel and zeolite.

7. A device as claimed in claim 1, wherein said gas detecting means comprises a semiconductor gas sensor.

8. A device as claimed in claim 1, wherein said gas detecting means is disposed in said gas container.

9. A device for measuring a gas dissolved in an oil sample, comprising:

a sample container for containing an oil sample;

an air bubble discharging means, provided in said sample container, for extracting a measurement gas dissolved in said oil sample;

a gas container for containing said measurement gas extracted by said air bubble discharging means;

gas detecting means for detecting said measurement gas charged in said gas container;

measuring means for measuring a concentration of said measurement gas in response to a signal dispatched from said gas detecting means;

pumping means for supplying air to said air bubble discharging means; and filter means for purifying the air before being fed into said air bubble discharging means;

said air bubble discharging means comprising a mesh filter having a mesh of 0.5 to 10 μm square for discharging bubbles therefrom and air leading means for leading air to said discharging means; wherein said sample container includes bubble eliminating means for eliminating air bubbles generated in said sample container.

10. A device as claimed in claim 9, wherein said bubble eliminating means comprises at least one net for passing the measurement gas and preventing the air bubble from passing therethrough.

11. A device as claimed in claim 10, wherein said gas container is expansible according to the amount of the measurement gas.

12. A device as claimed in claim 11, wherein said gas container comprises a rubber bag for accommodating the measurement gas and a hard case for encasing said rubber bag and regulating expansion of said rubber bag so that a predetermined amount of the measurement gas is accommodated therein.

13. A device as claimed in claim 11, wherein said gas container comprises a tedler bag.

14. A device as claimed in claim 1, said device further comprises switching means for controlling energization of said pumping means when the capacity of said gas container reaches the maximum.

15. A device as claimed in claim 1, wherein said measuring means comprises a resistance bridging circuit one side component of which is at least a part of said gas detecting means.

16. A device as claimed in claim 1, wherein said filter means is provided at the entrance of said air leading means.

17. A device as claimed in claim 16, wherein said filter means comprises a case having an inlet for introducing the air and an outlet for discharging the purified air and a filter body provided in said case for purifying the air.

18. A device as claimed in claim 11, wherein said gas container comprises a cylinder.

19. A device as claimed in claim 11, wherein said gas container comprises a bellows.

20. A device as claimed in claim 1, wherein said filter means comprises a case having an inlet for introducing the air and an outlet for discharging the purified air and a filter body provided in said case for purifying the air.

* * * * *